United States Patent [19]

Bohlen et al.

[11] Patent Number: 4,605,643

[45] Date of Patent: Aug. 12, 1986

[54] OVINE GRF

[75] Inventors: Peter Bohlen, Encinitas, Calif.; Paul E. Brazeau, Outremont, Canada; Frederick S. Esch, Oceanside, Calif.; Nicholas C. Ling; William B. Wehrenberg, both of San Diego, Calif.

[73] Assignee: The Salk Institute for Biological Studies, San Diego, Calif.

[21] Appl. No.: 585,814

[22] Filed: Mar. 2, 1984

[51] Int. Cl.$^4$ .................. A61K 37/43; C07K 7/10
[52] U.S. Cl. ................................ 514/12; 530/324
[58] Field of Search ............... 260/112.5 R; 514/12

[56] References Cited

U.S. PATENT DOCUMENTS 4,118,483 10/1978 König et al. ............... 260/112.5 R
4,395,400 7/1983 König et al. ............... 260/112.5 R

OTHER PUBLICATIONS

Wilson et al., *Neuroendocrinology*, 15, 313–327 (1974).
Yue et al., *Diabetes*, 24 (No. 7), 625–632 (1975).
Esch et al., *Biochemical and Biophysical Research Communications*, vol. 117, No. 3, 772–779 (1983).

*Chemical Abstracts*, vol. 81, 1974, Abst. No. 117701t.

*Primary Examiner*—Delbert R. Phillips
*Assistant Examiner*—F. T. Moezie
*Attorney, Agent, or Firm*—Fitch, Even, Tabin & Flannery

[57] ABSTRACT

A synthetic peptide is extremely potent in stimulating the release of pituitary GH in mammals, particularly in sheep, since it is the replicate of the native (hormone) releasing factor of the sheep hypothalamus. It contains the following sequence: Tyr-Ala-Asp-Ala-Ile-Phe-Thr-Asn-Ser-Tyr-Arg-Lys-Ile-Leu-Gly-Gln-Leu-Ser-Ala-Arg-Lys-Leu-Leu-Gln-Asp-Ile-Met-Asn-Arg-Gln-Gln-Gly-Glu-Arg-Asn-Gln-Glu-Gln-Gly-Ala-Lys-Val-Arg-Leu. This peptide or a biologically active fragment thereof, or analogs thereof having well-known substitutions and/or additions, as well as nontoxic salts of any of the foregoing, may be administered therapeutically to mammals and may be used diagnostically. The peptide is particularly useful in stimulating the release of GH so as to accelerate growth in warm-blooded non-human animals, particularly sheep, and/or to improve aquiculture.

12 Claims, No Drawings

OVINE GRF

This invention was made with Government support under grants HD-09690 and AM-18811 awarded by the National Institutes of Health. The Government has certain rights in this invention.

The present invention relates to a peptide having influence on the function of the pituitary gland in humans and other mammals. In particular, the present invention is directed to a peptide which promotes the release of growth hormone by the pituitary gland.

BACKGROUND OF THE INVENTION

Since the early 1950's, physiologists and clinicians have recognized that the hypothalamus of the brain controls all the secretory functions of the adenohypophysis. This control is neurohumoral, with specialized neurosecretory neurons in the hypothalamus producing special polypeptides, the effect and role of each of which is to trigger acutely and chronically the secretion of each pituitary hormone.

An inhibitory factor was earlier characterized in the form of hypothalamic somatostatin which inhibits, at the pituitary level, the secretion of growth hormone. In 1982, a corresponding hypothalamic releasing factor for pituitary growth hormone or somatotropin was isolated from a human islet cell tumor, purified, characterized and synthesized. When tested, it was found to promote the release of growth hormone(GH) by the pituitary. This peptide has the sequence:
H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu-NH$_2$. Human hypothalamic growth hormone releasing factor (hGRF) has now been found to have the same structure. Bohlen et. al. *Biochem. and Biophs. Res. Comm.*, 114, 3, pp. 930–936 (1983).

SUMMARY OF THE INVENTION

A 44-residue polypeptide has now been isolated from purified extracts of ovine hypothalami and characterized. It is found to have the amino acid formula: H-Tyr-Ala-Asp-Ala-Ile-Phe-Thr-Asn-Ser-Iyr-Arg-Lys-Ile-Leu-Gly-Gln-Leu-Ser-Ala-Arg-Lys-Leu-Leu-Gln-Asp-Ile-Met-Asn-Arg-Gln-Gln-Gly-Glu-Arg-Asn-Gln-Glu-Gln-Gly-Ala-Lys-Val-Arg-Leu-NH$_2$. It is believed to be and is hereinafter referred to as oGRF (for ovine growth hormone releasing factor) and will also be termed ovine somatocrinin. This peptide can be used to promote growth of warm-blooded animals, particularly sheep, of cold-blooded animals and in aquiculture. It may also be used to increase milk production in ewes in order to provide milk for making specialty cheeses.

Pharmaceutical compositions in accordance with the invention include oGRF, an analog thereof or a biologically active fragment thereof, or a nontoxic salt of any of the foregoing, dispersed in a pharmaceutically or veterinarily acceptable liquid or solid carrier. Such pharmaceutical compositions can be used in clinical medicine, both human and veterinary, in acute or chronic administration for diagnostic or therapeutic purposes. Moreover, they can be used to accelerate the growth of muscle mass in sheep or other animals.

DETAILED DESCRIPTION OF PREFERRED EMBODIMENTS

The nomenclature used to define the peptides is that specified by Schroder & Lubke, "The Peptides", Academic Press (1965), wherein in accordance with conventional representation the amino group at the N-terminal appears to the left and the carboxyl group at the C-terminal to the right. Where the amino acid residue has isomeric forms, it is the L-form of the amino acid that is represented unless otherwise expressly indicated.

The invention provides synthetic oGRF peptides having the following formula: H-Tyr-Ala-Asp-Ala-Ile-Phe-Thr-Asn-Ser-Tyr-Arg-Lys-Ile-Leu-Gly-Gln-Leu-Ser-Ala-Arg-Lys-Leu-Leu-Gln-Asp-Ile-Met-Asn-Arg-Gln-Gln-Gly-Glu-Arg-Asn-Gln-Glu-Gln-Gly-Ala-Lys-Val-Arg-Leu-Y wherein Y is OH or NH$_2$. Also included are biologically active fragments where Y can be either OH or NH$_2$.

The peptides can be synthesized by any suitable method, such as by exclusively solid-phase techniques, by partial solid-phase techniques, by fragment condensation, by classical solution couplings, or by the employment of recently developed recombinant DNA techniques. For example, the techniques of exclusively solid-phase synthesis are set forth in the textbook 37 Solid-Phase Peptide Synthesis", Stewart & Young, Freeman & Co., San Francisco, 1969, and are exemplified by the disclosure of U.S. Pat. No. 4,105,603, issued Aug. 8, 1978. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975). Production of the synthetic peptides using recombinant DNA techniques will likely be used to satisfy large-scale commercial requirements.

Synthesis by the use of recombinant DNA techniques, for purposes of this application, should be understood to include the suitable employment of a structural gene coding for a form of oGRF. The synthetic oGRF may be obtained by transforming a microorganism using an expression vector including a promoter and operator together with such structural gene and causing such transformed microorganism to express oGRF. A non-human animal may also be used to produce oGRF by gene-farming using such a structural gene and the general techniques set forth in U.S. Pat. No. 4,276,282 issued June 30, 1981 or using microinjection of embryos as described in WO83/01783 published 26 May 1983 and WO82/04443 published 23 December 1982. The synthetic oGRF may also be produced directly in the animal for which accelerated growth is intended by the techniques described in the two WO publications.

Common to coupling-type syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Also considered to be within the scope of the present invention are intermediates of the formula: $X^1$-Tyr($X^2$)-Ala-Asp($X^3$)-Ala-Ile-Phe-Thr($X^4$)-Asn-Ser($X^5$)-Tyr($X^2$)-Arg($X^6$)-Lys($X^7$)-Ile-Leu-Gly-Gln-Leu-Ser-($X^5$)-Ala-Arg($X^6$)-Lys($X^7$)-Leu-Leu-Gln-Asp($X^3$)-Ile-Met-Asn-Arg($X^6$)-Gln-Gln-Gly-Glu($X^3$)-Arg($X^6$)-Asn-Gln-Glu($X^3$)-Gln-Gly-Ala-Lys($X^7$)-Val-Arg($X^6$)-Leu-$X^8$ wherein: $X^1$ is either hydrogen or an α-amino protecting group. The α-amino protecting groups contemplated by $X^1$ are those known to be useful in the art of step-wise synthesis of polypeptides. Among the classes of α-amino protecting groups covered by $X^1$ are (1) acyl-type protecting groups, such as formyl, trifluoroacetyl, phthalyl, toluenesulfonyl(Tos), benzensulfonyl, nitrophenylsulfenyl, tritylsulfenyl, o-nitrophenoxyacetyl, chloroacetyl, acetyl, and γ-chlorobutyryl; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethyloxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl, and cyclohexyloxycarbonyl; (5) thiourethan-type protecting groups, such as phenylthiocarbonyl; (6) alkyl-type protecting groups, such as triphenylmethyl (trityl), benzyl;(7) trialkylsilane groups, such as trimethylsilane. The preferred α-amino protecting group is BOC.

$X^2$ is a protecting group for the phenolic hydroxyl group of Tyr selected from the group consisting of tetrahydropyranyl, tert-butyl, trityl, Bzl, CBZ, 4Br-CBZ and 2,6-dichlorobenzyl. The preferred protecting group is 2,6-dichlorobenzyl. $X^2$ can be hydrogen which means that there is no protecting group on the hydroxyl group.

$X^3$ is hydrogen or an ester-forming protecting group for the carboxyl group of Asp or Glu and is selected from the group consisting of Bzl, 2,6-dichlorobenzyl, methyl and ethyl.

$X^4$ and $X^5$ are protecting groups for the hydroxyl group of Thr and Ser and are selected from the group consisting of acetyl, benzoyl, tert-butyl, trityl, tetrahydropyranyl, Bzl, 2,6-dichlorobenzyl and CBZ. The preferred protecting group is Bzl. $X^4$ and/or $X^5$ can be hydrogen, which means there is no protecting group on the hydroxyl group.

$X^6$ is a protecting group for the guanidino group of Arg selected from the group consisting of nitro, Tos, CBZ, adamantyloxycarbonyl, and BOC, or is hydrogen;

$X^7$ is hydrogen or a protecting group for the side chain amino substituent of Lys. Illustrative of suitable side chain amino protecting groups are 2-chlorobenzyloxycarbonyl (2-Cl-Z), Tos, CBZ, t-amyloxycarbonyl and BOC.

The selection of a side chain amino protecting group is not critical except that it must be one which is not removed during deprotection of the α-amino groups during the synthesis. Hence, the α-amino protecting group and the side chain amino protecting group cannot be the same.

Optionally the side chain amido group of Gln and/or Asn can be suitably protected as with xanthyl (Xan).

$X^8$ is selected from the class consisting of OH, OCH$_3$, esters, amides, hydrazides, —O—CH$_2$-resin support and —NH-resin support, with the groups other than OH and amides being broadly considered as protecting groups.

In the formula for the intermediate, at least one of $X^1$, $X^2$, $X^3$, $X^4$, $X^5$, $X^6$, $X^7$, and $X^8$ is a protecting group.

In selecting a particular side chain protecting group to be used in the synthesis of the peptides, the following rules are followed: (a) the protecting group should be stable to the reagent and under the reaction conditions selected for removing the αamino protecting group at each step of the synthesis, (b) the protecting group should retain its protecting properties and not be split off under coupling conditions, and (c) the side chain protecting group should be removable, upon the completion of the synthesis containing the desired amino acid sequence, under reaction conditions that will not alter the peptide chain.

The peptides are preferably prepared using solid phase synthesis, such as that described by Merrifield, *J. Am. Chem. Soc.*, 85, p 2149 (1963), although other equivalent chemical syntheses known in the art can also be used as previously mentioned. Solid-phase synthesis is commenced from the C-terminal end of the peptide by coupling a protected α-amino acid to a suitable resin. Such a starting material can be prepared by attaching α-amino-protected Leu by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London) 38, 1597-98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp 1-6. BHA and MBHA resin supports are commercially available and are generally used only when the desired polypeptide being synthesized has an α-carboxamide at the C-terminal.

Leu protected by BOC is coupled to the chloromethylated resin according to the procedure of Monahan and Gilon, *Biopolymer* 12, pp 2513-19, 1973 when, for example, it is desired to synthesize the 44-amino acid peptide with free carboxy terminal. Following the coupling of BOC-Leu, the α-amino protecting group is removed, as by using trifluoroacetic acid(TFA) in methylene chloride, TFA alone or HCl in dioxane. The deprotection is carried out at a temperature between about 0° C and room temperature. Other standard cleaving reagents and conditions for removal of specific α-amino protecting groups may be used as described in Schroder & Lubke, "The Peptides", 1 pp 72-75 (Academic Press 1965).

After removal of the α-amino protecting group of Leu, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art.

Examples of suitable activating reagents are: (1) carbodiimides, such as N,N'-diisopropyl carbodiimide, N-N'-dicyclohexylcarbodiimide(DCCI); (2) cyanamides such as N,N'-dibenzylcyanamide; (3) keteimines; (4) isoxazolium salts, such as N-ethyl-5-phenyl isoxazolium-3'-sulfonate; (5) monocyclic nitrogen-containing heterocyclic amides of aromatic character containing one through four nitrogens in the ring, such as imidazolides, pyrazolides, and 1,2,4-triazolides. Specific heterocyclic amides that are useful include N,N'-carbonyl diimidazole, N,N'-carbonyl-di-1,2,4-triazole; (6) alkoxylated acetylene, such as ethoxyacetylene; (7) reagents which form a mixed anhydride with the carboxyl moiety of the amino acid, such as ethylchloroformate and isobutylchloroformate and (8) reagents which form an active ester with the carboxyl moiety of the amino acid, such as nitrogen-containing heterocyclic compounds having a hydroxy group on one ring nitrogen, e.g. N-hydroxyphthalimide, N-hydroxysuccinimide and 1-hydroxybenzotriazole(HOBT). Other activating reagents and their use in peptide coupling are described by Schroder & Lubke supra, in Chapter III and by Kapoor, *J. Phar. Sci.*, 59, pp 1–27 (1970).

Each protected amino acid or amino acid sequence is introduced into the solid phase reactor in about a two-fold or more excess, and the coupling may be carried out in a medium of dimethylformamide(DMF):CH$_2$Cl$_2$ (1:1) or in DMF or CH$_2$Cl$_2$ alone. In cases where incomplete coupling occurred, the coupling procedure is repeated before removal of the α-amino protecting group prior to the coupling of the next amino acid. The success of the coupling reaction at each stage of the synthesis is monitored by the ninhydrin reaction, as described by E. Kaiser et al., *Anal. Biochem.* 34, 595 (1970).

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$, $X^6$, $X^7$ and $X^8$ and the α-amino protecting group $X^1$, to obtain the peptide.

As an alternative route, the intermediate peptide may be separated from the resin support by alcoholysis after which the recovered C-terminal alkyl ester is converted to the acid by hydrolysis. Any side chain protecting groups may then be cleaved as previously described or by other known procedures, such as catalytic reduction (e.g. Pd on BaSO$_4$). When using hydrogen fluoride for cleaving, anisole and methylethyl sulfide are included in the reaction vessel for scavenging.

The following Example sets forth the preferred method for synthesizing oGRF by the solid-phase technique. It will of course be appreciated that the synthesis of a correspondingly shorter peptide fragment is effected in the same manner by merely eliminating the requisite number of amino acids at either end of the chain; however, it is presently felt that biologically active fragments should contain the indicated sequence at the N-terminal.

EXAMPLE I

The synthesis of oGRF(1-44) amide having the formula:

H-Tyr-Ala-Asp-Ala-Ile-Phe-Thr-Asn-Ser-Tyr-Arg-Lys-Ile-Leu-Gly-Gln-Leu-Ser-Ala-Arg-Lys-Leu-Leu-Gln-Asp-Ile-Met-Asn-Arg-Gln-Gln-Gly-Glu-Arg-Asn-Gln-Glu-Gln-Gly-Ala-Lys-Val-Arg-Leu-NH$_2$ is conducted in a stepwise manner using a Beckman 990 Peptide Synthesizer and an MBHA resin. Coupling of BOC-Leu to the resin is performed by the general procedure set forth in U.S. Pat. No. 4,292,313, and it results in the substitution of about 0.2–0.6 mmol Leu per gram of resin depending on the substitution of the MHBA resin used. All solvents that are used are carefully degassed by sparging with an inert gas, preferably helium, to insure the absence of oxygen that might undesirably oxidize the sulfur of the Met residue.

After deprotection and neutralization, the peptide chain is built step-by-step on the resin. Deprotection, neutralization and addition of each amino acid is performed in general accordance with the procedure set forth in detail in Guillemin et al. U.S. Pat. No. 3,904,594. The couplings are specifically carried out as set out in the following schedule.

SCHEDULE

| STEP | REAGENTS AND OPERATIONS | MIX TIMES MIN. |
|---|---|---|
| 1 | CH$_2$Cl$_2$ (2 times) | 0.5 |
| 2 | 50% trifluoroacetic acid (TFA) + 5% 1,2-ethanedithiol in CH$_2$Cl$_2$ (1 time) | 0.5 |
| 3 | 50% trifluoroacetic acid (TFA) + 5% 1,2-ethanedithiol in CH$_2$Cl$_2$ (1 time) | 20.0 |
| 4 | CH$_2$Cl$_2$ wash (3 times) | 0.5 |
| 5 | CH$_3$OH wash (2 times) | 0.5 |
| 6 | 10% triethylamine (Et$_3$N) in CH$_2$Cl$_2$ neutralization (2 times) | 0.5 |
| 7 | CH$_3$OH wash (2 times) | 0.5 |
| 8 | 10% triethylamine (Et$_3$N) in CH$_2$Cl$_2$ neutralization (2 times) | 0.5 |
| 9 | CH$_3$OH wash (2 times) | 0.5 |
| 10 | CH$_2$Cl$_2$ wash (2 times) | 0.5 |
| 11 | *Boc—amino acid (1 mmole/g resin) plus equivalent amount of dicyclohexylcarbodiimide (DCC) in CH$_2$Cl$_2$ | 120 |
| 12 | CH$_2$Cl$_2$ wash (1 time) | 0.5 |
| 13 | 50% dimethylformamide in CH$_2$Cl$_2$ wash (2 times) | 0.5 |
| 14 | 10% triethylamine (Et$_3$N) in CH$_2$Cl$_2$ wash (1 time) | 0.5 |
| 15 | CH$_3$OH wash (2 times) | 0.5 |
| 16 | CH$_2$Cl$_2$ wash (2 times) | 0.5 |
| 17 | 25% acetic anhydride in CH$_2$Cl$_2$ (2 ml/g resin) | 20.0 |
| 18 | CH$_2$Cl$_2$ wash (2 times) | 0.5 |
| 19 | CH$_3$OH wash (2 times) | 0.5 |

*For the coupling of Asn and Gln, an 1.136 molar excess of 1-hydroxybenzotriazole (HOBt) was included in this step.

Briefly, for the coupling reaction, one mmol. of BOC-protected amino acid in methylene chloride is used per gram of resin, plus one equivalent of 0.5 molar DCCI in methylene chloride or 30% DMF in methylene chloride, for two hours. When Arg is being coupled, a mixture of 10% DMF and methylene chloride is used. Bzl is used as the hydroxyl side-chain protecting group for Ser and Thr. 2-chloro-benzyloxycarbonyl (2Cl-Z) is used as the protecting group for the Lys side chain. Tos is used to protect the guanidino group of Arg, and the Glu or Asp carboxyl group is protected as the Bzl ester. The phenolic hydroxyl group of Tyr is protected with 2,6-dichlorobenzyl. At the end of the synthesis, the following composition is obtained: $X^1$-Tyr($X^2$)-Ala-Asp($X^3$)-Ala-Ile-Phe-Thr($X^4$)-Asn-Ser($X^5$)Tyr($X^2$)-Arg($X^6$)-Lys($X^7$)-Ile-Leu-Gly-Gln     Leu-Ser($X^5$)-Ala-Arg($X^6$)-Lys($X^7$)-Leu-Leu-Gln-Asp($X^3$)-Ile-Met-AsnArg($X^6$)-Gln-Gln-Gly-Glu($X^3$)-Arg($X^6$)-Asn- Gln-Glu($X^3$)-Gln-Gly-Ala-Lys($X^7$)-Val-Arg($X^6$)-Leu-$X^8$ wherein $X^1$ is BOC, $X^2$ is 2,6-dichlorobenzyl, $X^3$ is benyzl ester, $X^4$ is Bzl, $X^5$ is Bzl, $X^6$ is Tos, $X^7$ is 2Cl-Z and $X^8$ is -NH-MBHA resin support.

After the final Tyr residue has been coupled to the resin, the BOC group is removed with 45% TFA in CH$_2$Cl$_2$. In order to cleave and deprotect the remaining protected peptide-resin, it is treated with 1.5 ml. anisole, 0.25 ml. methylethylsulfide and 10 ml. hydrogen fluoride (HF) per gram of peptide-resin, at $-20°$ C. for one-half hour and at $0°$ C. for one-half hour. After elimination of the HF under high vacuum, the resin-peptide remainder is washed alternately with dry diethyl ether and chloroform, and the peptide is then extracted with degassed 2N aqueous acetic acid. Lyophilization of the acetic acid extract provides a white fluffy material.

The cleaved and deprotected peptide is then dissolved in 30% acetic acid and subjected to Sephadex G-50 fine gel filtration.

The peptide is then further purified by CM-32 carboxymethyl cellulose (Whatman) cation-exchange chromatography(1.8×18 cm., $V_{bed}$=50 ml.) using a concave gradient generated by dropping 1 L. of 0.4 M NH$_4$OAc, pH 6.5 into a mixing flask containing 400 ml. 0.01 M. NH40Ac, pH 4.5. Final purification is carried out using partition chromatography on Sephadex G-50 fine support (Pharmacia) with a nBuOH:EtOH:-pyridine:0.2% N HOAc (4'1:1:7) solvent system. Purification details are generally set forth in Ling et al. *Biochem. Biophys. Res. Commun.* 95, 945 (1980). The chromatographic fractions are carefully monitored by TLC, and only the fractions showing substantial purity are pooled.

The synthesis is repeated using a chloromethylated resin to produce the same peptide having a free acid C-terminus, generally following the procedure described in *Biopolymers*, 12, 2513-19 (1973) to link Leu to the chloromethylated resin.

EXAMPLE II

The peptide oGRF(1-44) is isolated from ovine hypothalami extracts which effect secretion in vitro of immunoreactive growth hormone by rat pituitary cells following the procedure described in *Biochem. Bioph. Res. Comm.*, Vol 116, 726-734 (1983) for the isolation of porcine and bovine hypothalamic GRFs, respectively. The starting material from which the peptide was derived was hypothalami from about 2100 sheep brains which were lyophilized. The hypothalami are boiled for two minutes, and after cooling, an equal volume of 0.6 M HCl containing enzyme inhibitors was added. They are then homogenized and centrifuged. The supernatant is defatted with petroleum ether and diethyl ether, and the aqueous phase is neutralized to pH 7.4. The salt concentration is then adjusted to about that of saline by dilution, and the liquid is then pumped through an Affi-Gel 10 (Bio Rad Laboratories) affinity column (7.2×3.5 cm.) that has been coupled to antibodies raised against hGRF. After washing off the unbound material, the adsorbed oGRF material is thereafter eluted from the column with 1 M acetic acid and then applied to a Sephadex G75 column (4.5×120 cm.). It is then eluted with 1 M. acetic acid containing 0.2% β-mercaptoethanol. The eluate fractions are assayed by testing their ability to release GH from rat pituitary cells in a monolayer culture as previously reported by Brazeau et. al. *P.N.A.S., USA*, 79, 7909-7913 (1982) and/or by using a heterologous RIA with antisera raised against hGRF(1-40). The bioreactive or immunoreactive fractions are then pumped onto a reverse phase semipreparative C18 column. Elution from this column is effected with 0.25M TEAP in an acetonitrile gradient. The major bioreactive or immunoreactive fraction is then applied to an analytical C18 column using a 0.2 vol % aqueous heptafluorobutyric acid/acetonitrile solvent system. Two bio- and immunoreactive fractions from this column, if not already pure, are further run on an analytical RP-HPLC C4 column using an 0.1% TFA/acetonitrile gradient to get two fractions of pure oGRF. The major fraction is tested as set forth hereinafter.

Amino acid analysis of the isolated peptide is carried out following hydrolysis in sealed tubes using methodology as described in *Anal. Biochem.*, 126, 144-156 (1982) using a Liquimat III amino acid analyzer, giving the following molar ratios: Asx(5), Thr(1), Ser(2), Glx(8), Gly(3), Ala(4), Val(1), Met(1), Ile(3), Leu(5), Tyr(2), Phe(1), Lys(3), and Arg(5). Sequencing of this isolated peptide from the major fraction gives the formula set forth hereinbefore.

The earlier eluting fraction has the same amino acid composition as the major fraction oGRF peptide described hereabove and is probably its methionineoxidized form.

EXAMPLE III

To determine the effectiveness of the peptide to promote the release of growth hormone, in vitro assays are carried out using synthetic hGRF(1-44)-NH$_2$ in side-by-side comparison with equimolar concentrations of the extracted and purified oGRF(1-44) of Example II. hGRF thus serves as a GRF Reference Standard having a known effectiveness to promote the release of growth hormone from rat pituitary cells. Cultures are used which include cells of rat pituitary glands removed some four to five days previously. Both cultures of a defined standard medium and cultures which are considered optimal for the secretion of growth hormone are used for the comparative testing, in the general manner described in Brazeau, et al. *Regulatory Peptides*, 1, 255, 1981. Incubation with the substance to be tested is carried out for 3 to 4 hours, and aliquots of the culture medium are removed and processed to measure their contents in immunoreactive GH(ir GH) by a well-characterized radioimmunoassay.

The results of this comparative testing shows that, in equimolar ratios, the oGRF(1-44) has the full intrinsic biological activity of the synthetic peptide and close to the same potency. In multiple doses factorial design experiments, oGRF is shown to have about the same intrinsic activity as hGRF(1-44)-NH$_2$ and a specific activity equal to about 70% of hGRF(1-44)-NH$_2$.

Approximately 1 out of 7000 to 15,000 children born in the USA are known to be pituitary growth hormone deficient or "pituitary-dwarfs", i.e., they are dwarfs because they lack the normal levels of pituitary GH in their blood. There are clinical reasons to propose that most of these patients have a normal pituitary gland and that the cause of their problem is a lack either of the synthesis, or of the secretion, of the hypothalamic releasing factor for GH. Synthetic oGRF may be used to treat these cases who have heretofore been treated by injections of human pituitary GH, an extremely expensive preparation obtained exclusively from human pituitaries at autopsies. Human GH prepared by DNA-recombinant methodology, though announced in the literature, is not currently available for routine use.

Synthetic oGRF may also be used as a routine test for GH secretion in cases in which a specific defect of pituitary function is suspected by a physician. Synthetic oGRF may also replace the cumbersome methods used currently (arginine infusions, hypoglycemia, L-DOPA injections, etc.) to assess GH secretory ability as a diagnostic procedure and may also be useful for other purposes recently postulated for hGRF.

For administration to humans, synthetic oGRF peptides should have a purity of at least about 93% and preferably at least 98%. This purity means the intended peptide constitutes the stated weight % of all like peptides and peptide fragments present. Most of the biologically active peptides have been found to possess biological activities other than those for which they were originally recognized. In view of such precedents, it is likely that oGRF will be found to possess extrapituitary activities which may be of practical interest.

Chronic administration of synthetic oGRF peptides to farm animals, particularly sheep, or other warm-blooded animals is expected to promote anabolism and thus increase body weight in terms of muscle mass. The use in veterinary medicine of the GRF of its species, i.e. oGRF in ovine, is the ideal situation since the molecule injected or otherwise administered will not be antigenic, being of the same species as that of the animal treated. It should also increase milk production in ewes. Use in aquiculture for raising fish and other cold-blooded marine animals to accelerate growth may also be important. Administration to animals at a purity as low as about 5% may be acceptable and will generally be carried out using a combination of the peptide and a veterinarily acceptable solid or liquid carrier to form what for purposes of this application is broadly termed a pharmaceutical composition.

Synthetic oGRF or the nontoxic salts thereof, combined with a pharmaceutically acceptable carrier to form a pharmaceutical composition, may be administered to mammals, including humans, either intravenously, subcutaneously, intramuscularly, intranasally or orally. The administration may be employed by a physician to stimulate the release of growth hormone where the host being treated requires such therapeutic treatment. The required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically-acceptable carrier.

Usually, the dosage will be from about 20 to about 2000 nanograms of the peptide per kilogram of the body weight of the host.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, modifications in the 44-member chain, particularly deletions beginning at the carboxyl terminal of the peptide, can be made in accordance with the known experimental evidence previously obtained with hGRF and following the practises to date to create fragments 34 to 43 residues in length, e.g. oGRF(1-40) and oGRF(1-37), or even shorter fragments, i.e. oGRF(1-32), which fragments may have either $NH_2$ or OH at the C-terminal that retain the intrinsic biological activity of the peptide, and such shorter peptides are considered as being within the scope of the invention. Moreover, additions can be made to either terminal, or to both terminals, and/or generally equivalent residues can be substituted for naturally occurring residues, as is well-known in the overall art of peptide chemistry to produce analogs having at least a substantial portion of the potency of the native polypeptide without deviating from the scope of the invention.

Particular features of the invention are set forth in the claims which follow.

What is claimed is:

1. A peptide having the formula: H-Tyr-Ala-Asp-Ala-Ile-Phe-Thr-Asn-Ser-Tyr-Arg-Lys-Ile-Leu-Gly-Gln-Leu-Ser-Ala-Arg-Lys-Leu-Leu-Gln-Asp-Ile-Met-Asn-Arg-Gln-Gln-Gly-Glu-Arg-Asn-Gln-Glu-Gln-Gly-Ala-Lys-Val-Arg-Leu-Y wherein Y is OH or $NH_2$ or a nontoxic salt of said peptide.

2. A synthetic peptide having the formula of claim 1 wherein Y is $NH_2$.

3. A synthetic peptide having the formula of claim 1 wherein Y is OH.

4. A composition for accelerating the growth of sheep comprising an effective amount of a peptide as defined in claim 2 and a veterinarily acceptable solid or liquid carrier therefor.

5. A composition for use in accelerating the growth of sheep comprising an effective amount of a peptide having the sequence: Tyr-Ala-Asp-Ala-Ile-Phe-Thr-Asn-Ser-Tyr-Arg-Lys-Ile-Leu-Gly-Gln-Leu-Ser-Ala-Arg-Lys-Leu-Leu-Gln-Asp-Ile-Met-Asn-Arg-Gln-Gln-Gly-Glu-Arg-Asn-Gln-Glu-Gln-Gly-Ala-Lys-Val-Arg-Leu or a nontoxic salt of said peptide, plus a veterinarily acceptable solid or liquid carrier therefor.

6. A method of accelerating the growth of sheep comprising administering an effective amount of a peptide having the sequence: Tyr-Ala-Asp-Ala-Ile-Phe-Thr-Asn-Ser-Tyr-Arg-Lys-Ile-Leu-Gly-Gln-Leu-Ser-Ala-Arg-Lys-Leu-Leu-Gln-Asp-Ile-Met-Asn-Arg-Gln-Gln-Gly-Glu-Arg-Asn-Gln-Glu-Gln-Gly-Ala-Lys-Val-Arg-Leu, or a nontoxic salt of said peptide.

7. A method in accordance with claim 6 wherein the carboxyl terminus is free acid.

8. A method in accordance with claim 6 wherein the carboxyl terminus is amide.

9. A method of stimulating the release of GH in sheep by administering intravenously, subcutaneously, intramuscularly, intranasally or orally about 20 to about 2000 nanograms of the peptide of claim 1 per kilogram of body weight.

10. A method of stimulating the release of GH in sheep by administering intravenously, subcutaneously, intramuscularly, intranasally or orally about 20 to about 2000 nanograms of the peptide of claim 2 per kilogram of body weight.

11. A method of stimulating the release of GH in sheep by administering intravenously, subcutaneously, intramuscularly, intranasally or orally about 20 to about 2000 nanograms of the peptide of claim 3 per kilogram of body weight.

12. A method of increasing muscle mass in sheep by administering intravenously, subcutaneously, intramuscularly, intranasally or orally about 20 to about 2000 nanograms of the Peptide of claim 1 per kilogram of body weight.

* * * * *

UNITED STATES PATENT AND TRADEMARK OFFICE
CERTIFICATE OF CORRECTION

PATENT NO. : 4,605,643
DATED : August 12, 1986
INVENTOR(S) : Peter Bohlen, et al.

It is certified that error appears in the above-identified patent and that said Letters Patent is hereby corrected as shown below:

Column 1, line 47, Change "Iyr" to --Tyr--.

Column 2, line 26, Change "37" to --"--.

Column 3, line 16, Correct the spelling of "benzene sulfonyl".

Column 4, line 12, Change "αamino" to --α-amino--.

Column 6, line 24, After "$CH_2Cl_2$" insert --wash--.

Column 7, line 26, Change "NH40Ac" to --$NH_4OAc$--,

Column 7, line 29, Change "4'" to --4:--,

Column 7, line 46, After "(1983)" insert --and Vol. 117 772-779 (1983)--.

Column 10, line 51, Change "AIa" to --Ala--.

Column 12, line 5, After "muscle" delete period,

Column 12, line 8, Change "Peptide" to --peptide--.

Signed and Sealed this

Thirtieth Day of December, 1986

Attest:

DONALD J. QUIGG

Attesting Officer   Commissioner of Patents and Trademarks